United States Patent [19]

Kruse

[11] Patent Number: 4,831,209
[45] Date of Patent: May 16, 1989

[54] FRACTIONATION FOR A $C_6$ PARAFFIN ISOMERIZATION PROCESS

[75] Inventor: Larry W. Kruse, Crete, Ill.

[73] Assignee: Amoco Corporation, Chicago, Ill.

[21] Appl. No.: 206,357

[22] Filed: Jun. 14, 1988

[51] Int. Cl.[4] .............................................. C07C 5/13
[52] U.S. Cl. ................................................. 585/738
[58] Field of Search ........................................ 585/738

[56]  References Cited
  FOREIGN PATENT DOCUMENTS
  789057  7/1968  Canada ................................ 585/738

Primary Examiner—Curtis R. Davis
Attorney, Agent, or Firm—Robert E. Sloat; William M. Magidson; Ralph C. Medhurst

[57] ABSTRACT

A paraffin isomerization zone is described wherein an improvement to the process comprises using a preflash tower in connection with stabilizer and de-isohexanizer towers to efficiently separate the isomerization zone effluent into valuable components having higher octane values and a recycle material which can be reintroduced along with a fresh feed into the isomerization zone reactor.

6 Claims, 2 Drawing Sheets

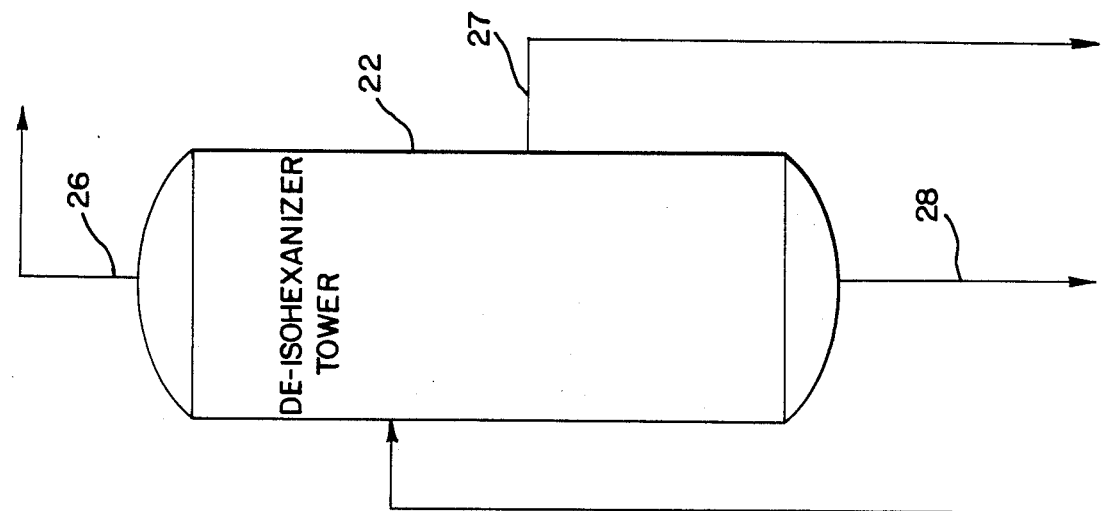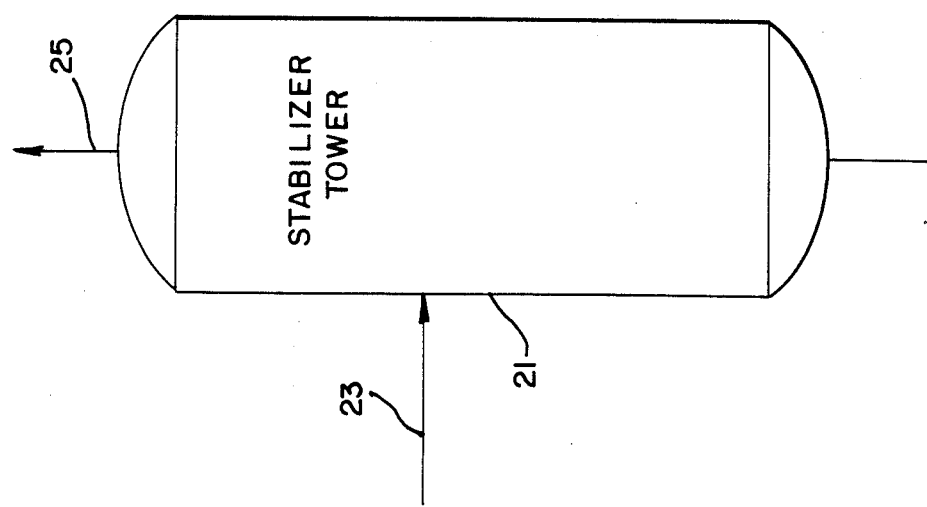
FIG. 2

FRACTIONATION FOR A C$_6$ PARAFFIN ISOMERIZATION PROCESS

BACKGROUND OF THE INVENTION

1. Field of the Invention

This invention relates to C$_6$ paraffin isomerization in which a preflash tower is used to initially separate liquid product from the isomerization zone.

2. General Background

Paraffin isomerization processes are generally used in modern refineries to enhance the octane value of paraffinic and cycloparaffinic hydrocarbons having from 4 to about 7 carbon atoms. The product from the isomerization zone is normally fed to a fractionation section where selected C$_5$ and C$_6$ paraffins and cycloparaffins which have increased octane are concentrated and sent to the refinery gasoline pool. The less desirable or low octane liquids are generally recycled to the isomerization zone. A small portion of the heaviest materials produced in the isomerization zone is generally removed from the process as a slip stream, and light gaseous materials are sent to the refinery fuel gas system.

The typical fractionation scheme for an isomerization zone includes a high pressure separation zone which separates the effluent from the isomerization zone into light gases and an isomerization zone liquid effluent. The latter is recovered and sent to a fractionation section.

In cases where there is no recycle to the isomerization zone (once through operations) the liquid effluent from the separation zone is passed into a stabilizer tower which separates fuel gas from liquid isomerization zone product which has enhanced octane value and can be used in the gasoline pool.

In many isomerization operations, some of the low octane effluent from the isomerization zone is separated from valuable isomerization zone product and recycled to the isomerization zone for additional conversion. These operations are generally known as recycle operations. The fractionation section design in these conventional operations can vary, but in most instances when a new isomerization unit is being built, the fractionation section will comprise two separate towers.

In conventional two tower recycle operations in which no preflash tower is used (see FIG. 2), the first tower is a stabilizer tower into which all the liquid effluent from the separation zone is passed and separated into fuel gas comprising C$_3$ and lighter hydrocarbons and a stabilizer tower bottoms stream which contains essentially all of the remaining liquid effluent from the separation zone. The liquid feed rate to the stabilizer tower in the above operation is much larger than the liquid feed rate to this tower when operated in once-through operations, since recycle material is contained in feed.

The bottoms stream from the stabilizer tower is then fed into a de-isohexanizer tower for separation into the following three streams: the lightest stream is generally the isomerization zone product having enhanced octane value which is recovered from the overhead section of the de-isohexanizer tower and sent to the refinery gasoline pool; a side stream is drawn off comprising recycle material which comprises C$_6$ and some C$_7$ hydrocarbons; and a bottoms stream generally comprising the heaviest components produced in the isomerization zone is generally purged from the system to avoid buildup of these heavier materials.

When a refiner designs a grass-root paraffinic isomerization zone for once-through operations or recycle operations, he has much flexibility in reactor designs along with the sizing of the various towers used in the fractionation section of the isomerization zone process.

In instances in which the refiner desires to alternately operate an isomerization zone in either the once-through or recycle modes, various compromises must be made in the fractionation section in order to provide adequate sizing of both stabilizer and de-isohexanizer towers for these two different operations. In the once-through operation, since there is no recycle of unreacted material to the isomerization zone reactor the stabilizer tower will receive a lower feed rate of liquid effluent when compared to the feed rate of liquid effluent it would receive during recycle operation. In many instances these compromises will result in less than ideal separations or design of tower reboilers or heat exchangers. Costs will not be optimized because the stabilizer tower must be designed for a wide range of flow rates and operating conditions.

The present invention offers an improvement to the refiner having a paraffin isomerization process designed to operate alternately in either the once-through or recycle mode, and which is either being built as a grass-roots project or is a revamp using some existing equipment. In the present invention a process improvement results from the use of a preflash tower during recycle operations to make a gross separation of the separation zone liquid effluent into preflash overhead fraction which contains substantial quantities of isomerization zone product and a preflash bottoms fraction. The latter fraction contains much of the unconverted C$_5$, C$_6$ and C$_7$ materials which boil at higher temperatures than the isomerization zone product, some isomerization zone product and a heavy stream comprising C$_6$+ materials. This stream is passed into the de-isohexanizer tower for further separation into three major streams.

The three streams are a de-isohexanizer tower overhead fraction which contains concentrated quantities of isomerization zone product which were not separated from the preflash tower bottoms fraction, a middle boiling stream comprising C$_5$ and C$_6$ recycle materials which are returned to the isomerization zone for further conversion, and a heavy stream comprising C$_6$+ materials which are removed from the process to avoid buildup within the processing loop.

The de-isohexanizer zone overhead fraction is combined with the preflash overhead fraction and passed into the stabilization tower. These two streams having been initially sent to the preflash tower now have a reduced quantity of heavier materials resulting in a lower quantity of feed material for the stabilizer tower to process. In the stabilization tower a separation of fuel gas from isomerization product takes place.

By using the preflash tower during recycle operations, the feed rates to both the stabilization tower and the de-isohexanizer tower are reduced since the preflash tower performs an initial liquid-liquid separation on the separation zone liquid. The stabilizer tower, can therefore, be designed for lower feed rates.

The reduced size of the stabilizer tower still allows its use in once-through operations, since in once-through operations a reduced quantity of liquid effluent from the isomerization zone is passed into the fractionation section. In once-through operations, the liquid effluent from the separation zone passes directly to the stabilizer tower for separation into fuel gas and isomerization zone product.

SUMMARY

The present invention can be summarized as an improved isomerization process in which liquid effluent from an isomerization zone is passed through a preflash tower to separate the effluent into an overhead fraction comprising dimethylbutane, pentanes, and lighter materials and a preflash bottoms fraction comprising dimethylbutane, pentanes, and heavier materials prior to these fractions passing into stabilizer and de-isohexanizer towers.

It is the object of the present invention to provide an improved paraffin isomerization process wherein the fractionation section of the process utilizes a preflash tower to reduce the liquid loads to downstream stabilizer and de-isohexanizer towers so they can be designed in a more economical fashion.

It is another object of the present invention to provide an improved process utilizing existing equipment when revamping an existing processing unit to a paraffin isomerization zone by using a preflash tower in situations where either a stabilization tower or a de-isohexanizer tower already exist and in which either of these towers is of too small a design to handle the liquids which would normally be passed to either of these towers in the absence of the use of the improved invention.

BRIEF DESCRIPTION OF THE DRAWINGS

Attached FIG. 1 shows an overall process flow scheme for the process of the present invention employing a preflash tower and FIG. 2 shows a conventional recycle operation employing stabilizer and de-isohexanizer towers.

Figure 1:
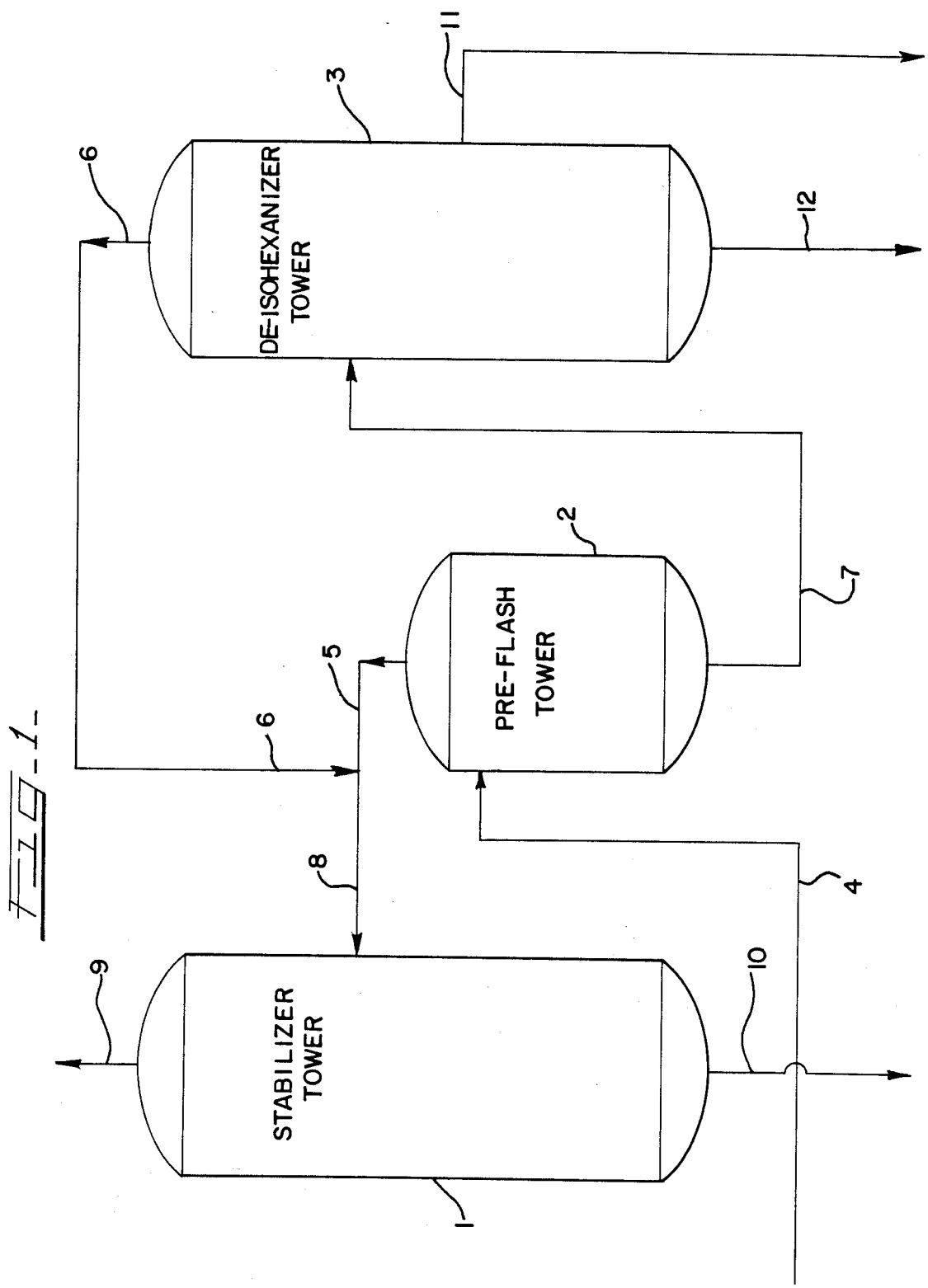

Shown in the drawing is stabilizer tower 1, preflash tower 2, and de-isohexanizer tower 3. These three fractionation towers are combined in a manner to allow the separation of liquid effluent derived from a paraffin isomerization zone into fuel gas, isomerization zone product, and other streams.

A liquid isomerization zone fresh feed stock which comprises $C_5$ through $C_6$ paraffins is combined with recycle stream 11 which is derived from the de-isohexanizer tower. These two liquid streams, combined with recycled hydrogen, pass into a state-of-the-art paraffin isomerization zone where the lower octane paraffins are converted to higher octance value materials. The effluent leaving the isomerization zone reactor is passed into a high pressure separator, or separation zone, for removal of light gases from liquid effluent. The resulting liquid effluent is then passed through line 4 into the preflash tower.

The liquid effluent passing through line 4 and into the preflash tower as preflashed tower feed generally will be a full range boiling material, boiling within a range of from about 80° F. to 170° F. or more and will contain large quantities of isopentanes, normal pentanes, dimethylbutanes, methylpentanes and $C_6$ normal and cycloparaffins.

In the preflash tower a gross separation of $C_5$ and $C_6$ paraffins occur. The preflash overhead fraction comprises dimethylbutanes, pentanes and lighter materials while the preflash bottoms fraction comprises dimethylbutanes, pentanes, and heavier materials.

The preflash tower bottoms fraction passes through line 7 into the de-isohexanizer tower 3 where it can be separated into three fractions—a de-isohexanizer overhead fraction, a side stream referred to as recycled material and a de-isohexanizer bottoms fraction generally comprising the heaviest materials contained in the feed to this tower.

The function of the de-isohexanizer tower is to recover as much as possible of the remaining isomerization zone product from the preflash tower bottoms fraction. Additionally, this tower recovers a recycle material which is combined with the fresh feed and returned to the isomerization zone for additional conversion to more valuable, higher octane materials. The de-isohexanizer tower produces a heavy stream as a bottoms fraction, which can be removed from the process. It comprises heavy materials which can build up within the process loop if not removed from the process.

The de-isohexanizer overhead fraction passes through line 6 and can be combined with the preflash tower overhead fraction passing through line 5 and eventually passed through line 8 into the stabilizer tower 1. Some of either the materials passing through lines 5 or 6 may be removed from the process for other uses. These streams may also be added as separate streams to the stabilizer tower. It is not critical whether these overhead streams from the preflash and de-isohexanizer towers are combined or added separately to the stabilizer tower.

In the stabilizer tower a separation occurs on the materials flowing through line 8. Fuel gas removed from the overhead of the stabilizer tower comprises essentially $C_3$ and $C_4$ gaseous hydrocarbons. The preflash tower bottoms product comprises isomerization zone product and contains a full range of $C_5$ and $C_6$ hydrocarbons having enhanced octane values. Specifically this material will contain large quantities of isopentanes, dimethylbutanes, methylpentanes and other $C_6$ hydrocarbons. This material can add enhanced octane values to a normal refiner's gasoline pool and is the primary and most valuable product recovered from the fractionation zone described above when used in connnection with the paraffin isomerization zone process.

Shown in FIG. 2 is a conventional recycle flow scheme employing stabilizer and de-isohexanizer towers in which no preflash tower is used.

Liquid effluent from the separation zone passes through line 23 into stabilizer tower 21 where fuel gas is removed via line 25 and a stabilizer bottoms fraction then passes through line 24 into the de-isohexanizer tower 22.

In tower 22, three streams are recovered. An isomerization zone product is recovered as overhead stream 26, a recycle stream 27 is recovered and returned to the isomerization zone, and a heavy stream is recovered from line 28.

In this case the stabilizer tower needs to be designed to have a larger quantity of feed passing into it through line 23, since there is no preflash tower to make the gross separation of $C_5$ and $C_6$ materials as in the scheme shown in FIG. 1.

DESCRIPTION OF THE PREFERRED EMBODIMENT

In a broad embodiment, the present invention comprises:

A process for isomerizaton of a $C_5$ to $C_6$ feedstock comprising paraffins in which the feedstock is passed into an isomerization zone at reaction conditions to effect production of an effluent, containing an isomerization product having an increased octane value, wherein the effluent is passed into a separation zone for removal of light gases from liquid effluent, the liquid effluent is fractionated into (1) a fuel gas stream, (2) isomerization zone product comprising iso $C_5$ and iso $C_6$ paraffins, (3) a recycle stream comprising $C_6$ paraffins and cycloparaffins having higher boiling points than the isomerization zone product, a part of which is passed into the isomerization zone as recycle material and (4) a heavy stream comprising $C_6$ and $C_7$ and higher paraffins having a boiling range higher than recycle material, wherein an improvement comprises: (A) passing at least a portion of liquid effluent into a preflash tower for separation into a preflash overhead fraction comprising dimethylbutane, pentanes and lighter materials and a preflash bottoms fraction comprising dimethylbutane, pentanes and heavier materials, (B) passing at least a portion of the preflash bottoms fraction into a de-isohexanizer tower to separate said bottoms into a (i) de-isohexanizer overhead fraction comprising dimethylbutane, pentanes and lighter materials carried over into the di-isohexanizer column from the preflash tower, (ii) said recycle stream, and (iii) said heavy stream, (C) passing at least a portion of the preflash overhead fraction and the de-isohexanizer overhead fraction into a stabilizer tower to separate these fractions into (i) a fuel gas stream comprising $C_4$ and lighter hydrocarbons and (ii) said isomerization zone product.

The preflash tower, stabilization tower, and the de-isohexanizer towers as contemplated in the present invention can be of any normally acceptable design. In particular, these towers are typically fractionation towers which can include requisite amounts of trays and packing, if required, to enable the separations as described in the claims to take place.

In order to economically construct and operate the claimed process it is desirable that the three towers be designed to have a minimal excess capacity. Accordingly, the diameters and tower lengths and tray efficiencies of these units should be designed so as to provide maximum separation for each of the separation steps required with a minimum use of energy in all cases.

Typically, the fractionation towers will have control schemes including reflux and temperature controllers to allow the particular tower to be operated in an acceptable manner. The towers will also have sufficient feed and effluent exchangers when required, reboiler capacity, cooling capacity and reasonably quick response time to allow acceptable and safety controlled operations.

The isomerization zone is typically a paraffin isomerization zone well known to those in the art. This zone will generally contain a catalyst containing a platinum group metal and/or other metals and often times it is promoted by chloride or chloride addition to enhance the acidity of the catalyst within the isomerization zone.

The main purpose of the paraffin isomerization zone is to isomerize the $C_5$ through $C_6$ paraffins which are fed to this zone increasing their octane value.

Typical paraffin isomerization zone reaction conditions will operate at liquid hourly space velocities of anywhere from less than 1 to 4 or more, reaction temperatures anywhere from 150° F. up to 550° F. or more depending on the type of catalyst used in the zone, reactor pressures can vary anywhere from 100 to 1000 psig or more. Some isomerization reaction zones operate at lower temperatures to take advantage of equilibrium considerations but at the expense of conversion.

Isomerization zone reaction conditions also can include recycle of $C_5$ and $C_6$ paraffins which have not been converted to more valuable high octane materials and recycle and make-up hydrogen which are normally used.

The boiling ranges given for the various streams are generally the nominal initial and end boiling points and are not meant to unduly restrict the type of materials characterized by the boiling range. The particular materials characterized by boiling range will generally have most or the majority of their weight boiling within the stated boiling range. In a preferred instance, 75 percent by weight or more of the particular material will boil in this stated range.

In many instances, especially the lighter fractions and the heavier fractions, initial boiling point or end boiling point tails of substantial temperature ranges can occur. These tails can extend the boiling range by as much as 100° F. or more even though the materials causing the tail may be present in very small concentrations. This is most readily apparent when describing the boiling range of the de-isohexanizier heavy stream.

The isomerization zone feedstock generally will comprise $C_5$ and $C_6$ paraffins (normal iso and cycloparaffins) and will have a boiling range of anywhere from 80° F. to about 170° F. This stream generally represents a fresh feed component and a recycle stream and is generally passed to the isomerization zone with these two materials combined along with make-up hydrogen and recycle gas.

The isomerization zone liquid recycle material which is a portion or all of the recycle stream obtained from the de-isohexanizer tower generally boils in the range from about 140° up to about 160° F. and will comprise $C_6$ hydrocarbons such as dimethylbutanes, methylpentanes, normal hexanes, methylcyclopentanes and cyclohexanes. A typical recycle stream will contain about 60 percent of $C_6$ paraffins and as much as 25 percent cyclohexanes with the remaining materials being lighter weight components.

The hydrogen make-up which is also mixed with the feedstock passing into the isomerization zone will generally have at least 75 percent by volume gaseous hydrogen. The hydrogen recycle stream which is recovered from the initial separation of effluent leaving the isomerization zone will generally be of lower quality hydrogen. The isomerization zone effluent is passed into a separation zone for the first gross removal of high pressure gas materials from the remaining liquid. The light gas removed from the separation zone will generally comprise $C_3$ and lighter hydrocarbons and hydrogen.

The remaining liquid effluent that leaves the separation zone is the feedstock for the preflash tower. In most refining operations essentially all the liquid recovered from the separation zone will be passed into the preflash tower unless the refiner desires to add additional materials or remove a part of the liquid effluent recovered from the separation zone for other purposes.

The liquid effluent (preflash tower feedstock) generally comprises $C_5$ and $C_6$ paraffins and boils in the general range of from about 80° F. to about 170° F. This material will contain iso, normal and cyclopentanes along with dimethylbutanes, methylpentanes, normal hexanes, methylcyclopentanes and cyclohexanes in various concentrations. The concentrations of these materials are dictated in part by the extent to which equilibrium is reached in the isomerization reaction zone.

A typical liquid effluent passed into the preflash tower as feed will contain about 27 percent by weight of iso, normal and cyclopentanes and as much as 68 percent by weight of $C_6$ hydrocarbons.

In the preflash tower a gross separation takes place between a predominantly $C_5$ and a predominantly $C_6$ fraction of the feed to this tower.

The preflash overhead fraction will generally boil in the range of from about 80° F. to about 120° F. and will contain some $C_3$ and some $C_4$ normal gaseous materials along with iso, normal and cyclopentanes along with $C_6$ hydrocarbons such as dimethylbutane, methylpentane, normal hexane, methylcyclopentane and cyclohexane in various concentrations. The typical preflash tower overhead fraction will contain as much as 40 weight percent of $C_5$ hydrocarbons, and as much as 10 weight percent $C_4$ and lighter materials. The remaining components are $C_6$ hydrocarbons, such as dimethylbutanes, methylpentanes, normal hexane, methylcyclopentane and cyclohexane.

Since the preflash tower is designed only to provide a gross separation of $C_5$ and $C_6$ components, the preflash bottoms fraction leaving the preflash tower will also contain some quantities of the components contained in the preflash overhead fraction along with additional heavier materials. This fraction will generally boil in a higher range of from about 80° F. to about 170° F.

A portion or all of the preflash bottoms fraction is passed into the de-isohexanizer tower for separation into three streams. In this tower a more efficient separation takes place between a di-isohexanizer overhead fraction which will contain $C_5$ and $C_6$ hydrocarbons which represent a valuable component of the isomerization zone product. The de-isohexanizer overhead fraction will boil anywhere from about 80° F. to about 150° F.

A side draw from the de-isohexanizer tower is the recycle stream, all or a part of which can be recycled to the isomerization zone with feed for additional conversion into a valuable isomerization zone product. This stream will generally boil in a range of from about 120° F. to about 160° F. and will contain essentially all $C_6$ hydrocarbons. These materials will generally represent dimethylbutane, methylpentane, normal hexane, methylcyclopentane and cyclohexane. Depending upon the operation of this tower, the initial and end boiling points of this stream can vary. If for instance the refiner desires to take more of the recycle stream to the overhead fraction the recycle stream will contain higher boiling materials. Conversely, if the refiner desires to take more of the recycle stream to the bottom of the de-isohexanizer tower, it will be a material having a lighter hydrocarbon composition and will not boil in as high as stated temperature range.

The de-isohexanizer heavy stream is a bottom stream which is removed from the de-isohexanizer tower. This material generally will boil in a range of anywhere from 140° F. to 170° F. or more and will contain $C_6$ hydrocarbons in addition to $C_7+$ hydrocarbons. These materials will generally comprise methylpentane, normal hexane, methylcyclopentane, cyclohexane and any hydrocarbons having 7 carbon atoms or more in their chain or ring structure.

The feed to the stabilizer tower generally comprises the preflash overhead fraction combined with the de-isohexanizer tower overhead fraction and in most cases will include all these materials.

The stabilizer tower effects a removal of fuel gas components which generally comprise $C_3$ and $C_4$ materials from isomerization zone product. The fuel gas is removed as an overhead fraction of the stabilizer tower and the isomerization zone product is removed as a bottoms fraction from the stabilizer tower. The isomerization zone product generally will boil in a range of from about 80° F. to about 160° F. and comprises $C_5$ and $C_6$ hydrocarbons. It will contain such material isopentane, normal pentane, cyclopentane, dimethylbutane, methylpentane and normal $C_6$ hydrocarbons. The normal pentanes and hexanes are generally in fairly low concentrations in this stream, since the purpose of the isomerization zone is to reduce these relatively low octance materials by their conversion to higher octane materials.

A typical isomerization zone product can contain 32 weight percent of isopentane and up to 53 percent or more of iso $C_6$ hydrocarbons with the remaining material being heavier or lighter materials.

When substantially all of a stream is passed to a part of the fractionation section, only minor quantities are divereted to uses other than as described and claimed herein. In some cases small portions of the various streams can themselves be used as products.

EXAMPLE I

In this Example a fractionation section for a paraffin isomerization reaction zone arranged, as described in FIG. 1, was simulated to illustrate one embodiment of the invention. A commercial unit having this design is successfully operating.

The preflash towner had an inside diameter of 11 feet and an overall length (tangent to tangent) of approximately 30 feet. It contained slotted ring packing and had five theoretical trays. The preflash feed after heat exchange entered the tower at a temperature of 176° F., the preflash tower overhead fraction, prior to heat exchange, left the tower at a temperature of 272° F., and the preflash tower bottoms fraction, prior to heat exchange, left the tower at a temperature of 313° F. This tower was operated at a pressure of 170 psig at the overhead fraction exit.

The de-isohexanizer tower had an inside diameter of 12.5 feed and an overall length (tangent to tangent) of 115 feet. It contained sixty trays which were of a valve tray design. The feed to this tower, from the preflash tower, after heat exchange entered the tower at a temperature of 217° F., the de-isohexanizer tower overhead left the tower, prior to heat exchange, at a temperature of 195° F., the recycle stream left the tower, prior to heat exchange, at a temperature of 240° F., and the heavy stream left this tower prior to heat exchange, at a temperature of 258° F. This tower was operated at a pressure of 35 psig at the overhead fraction exit.

The stabilizer tower had an inside diameter of seven feet and an overall length (tangent to tangent) of 70.25 feet. It contained 24 trays which were of a valve tray design. The feed to this tower, after heat exchange, comprised the preflash and de-isohexanizer tower overhead fractions and was at a temperature of 270° F., the fuel gas stream leaving the stabilizer, before heat exchange, was at a temperature of 168° F., and the isomerization zone product leaving the stabilizer tower as a bottoms fraction, before heat exchange, was at a temperature of 284° F. This tower operated at an overhead pressure of 140 psig.

Table I below shows the various components passing through the fractionation section.

TABLE I

| Description wt. % | Stream No. | | | | | | | |
|---|---|---|---|---|---|---|---|---|
| | 4 Liquid Effluent | 5 PFT Overhead | 6 DIHT Overhead | 7 PFT Bottoms | 9 Fuel Gas | 10 IZ Product | 11 DIHT Recycle Stream | 12 DIHT Heavy Stream |
| $C_4-$ | 4.6 | 14.9 | 0.8 | 0.6 | 93.7 | 1.4 | — | — |
| i $C_5$ | 20.1 | 30.8 | 30.2 | 15.9 | 5.9 | 32.0 | — | — |
| n $C_5$ | 5.7 | 7.3 | 9.6 | 5.0 | 0.4 | 9.1 | — | — |
| Cyclo $C_5$ | 1.3 | 1.2 | 2.3 | 1.3 | — | 1.9 | 0.3 | — |
| 2,2 Dimethyl butane | 24.8 | 19.9 | 37.6 | 26.7 | — | 31.8 | 15.6 | 2.0 |
| 2,3 Dimethyl butane | 6.4 | 4.2 | 5.1 | 7.3 | — | 5.0 | 10.2 | 4.0 |
| 2 Methyl pentane | 17.4 | 11.1 | 10.8 | 20.0 | — | 11.6 | 31.2 | 15.1 |
| 3 Methyl pentane | 9.7 | 5.7 | 3.3 | 11.3 | — | 4.6 | 20.5 | 15.7 |
| n $C_6$ | 5.8 | 3.1 | 0.4 | 7.0 | — | 1.7 | 13.8 | 20.4 |
| Methyl cyclo pentane | 1.9 | 0.9 | — | 2.3 | — | 0.5 | 4.4 | 10.2 |
| Cyclo $C_6$ | 1.9 | 0.7 | — | 2.4 | — | 0.3 | 3.5 | 25.8 |
| Benzene + | 0.4 | 0.1 | — | 0.4 | — | — | 0.5 | 6.7 |
| Relative mass flow rate | 44.8 | 12.8 | 16.8 | 32.0 | 1.8 | 27.8 | 14.2 | 1.0 |
| volumetric flow rate, B/D | 40,873 | 12,268 | 15,318 | 28,605 | — | 25,415 | 12,437 | 838 |

Where:
PFT = preflash tower
DIHT = de-isohexanizer tower
IZ = isomerization zone The stabilizer tower in this Example had a total feed rate of 27,586 barrels/day of liquid (12,268 barrels/day of preflash tower overhead plus 15,318 barrels/day of de-isohexanizer tower overhead). The flow rate of isomerization zone tower product recovered from this tower was 25,415 barrels/day. The total liquid feed rate to the preflash tower in this Example was 40,873 barrels/day.

EXAMPLE II

In this Example a fractionation section for a paraffin isomerization zone was simulated in a once-through operation.

Liquid effluent from the separation zone was passed directly into the same stabilizer tower described in Example I which separated a fuel gas overhead from a bottoms fraction which represented isomerization zone product.

The de-isohexanizer tower was not used since no recycle to the isomerization zone was used.

A commercial unit was operated having this design. Table II below shows the various components passing through the fractionation section.

TABLE II

| Description wt. % | Stream | | |
|---|---|---|---|
| | Stabilizer Feed | Fuel Gas | Isomerization Zone Product |
| $C_4-$ | 5.2 | 96.6 | 1.4 |
| i $C_5$ | 29.6 | 3.2 | 30.8 |
| n $C_5$ | 7.9 | 0.2 | 8.2 |
| Cyclo $C_5$ | 1.8 | — | 1.9 |
| 2,2 Dimethyl butane | 20.0 | — | 20.8 |
| 2,3 Dimethyl butane | 5.2 | — | 5.4 |
| 2 Methyl pentane | 14.0 | — | 14.6 |
| 3 Methyl pentane | 7.8 | — | 8.1 |
| n $C_6$ | 4.7 | — | 4.9 |
| Methyl cyclo pentane | 1.7 | — | 1.7 |
| Cyclo $C_6$ | 1.7 | — | 1.7 |
| Benzene + | 0.4 | — | 0.5 |
| Relative Mass | 24.1 | 1.0 | 23.1 |

TABLE II-continued

| Description wt. % | Stream | | |
|---|---|---|---|
| | Stabilizer Feed | Fuel Gas | Isomerization Zone Product |
| flow ratio Volumetic flow rate B/D | 27,996 | | 26,433 |

The stabilizer tower in this Example had a feed rate of 27,996 barrels/day of liquid. About 26,433 barrels/day of isomerization zone product was recovered from the stabilizer tower.

EXAMPLE III

In this Example a conventional fractionation section was simulated for recycle operation. This operation did not use a preflash tower and illustrates operations which might be used in situations where a refiner is designing a fractionation section as a grass-roots project.

The flow scheme for this Example is shown in FIG. 2. Table III shows the stream compositions simulated for this Example. The liquid effluent fed to the stabilizer tower in this Example was assumed to have the same composition as the liquid effluent in Example I and the same volumetric flow rates were also used.

TABLE III

| Description wt. % | Stream No. | | | | |
|---|---|---|---|---|---|
| | 23 Liquid Effluent | 25 Fuel Gas | 26 IZ Product | 27 DIHT Recycle Stream | 28 DIHT Heavy Stream |
| $C_4-$ | 4.6 | 93.7 | 1.4 | — | — |
| i $C_5$ | 20.1 | 5.9 | 32.0 | — | — |
| n $C_5$ | 5.7 | 0.4 | 9.1 | — | — |
| Cyclo $C_5$ | 1.3 | — | 1.9 | 0.3 | — |
| 2,2 Dimethyl butane | 24.8 | — | 31.8 | 15.6 | 2.0 |
| 2,3 Dimethyl butane | 6.4 | — | 5.0 | 10.2 | 4.0 |
| 2 Methyl penta | 17.4 | — | 11.6 | 31.2 | 15.1 |
| 3 Methyl pentane | 9.7 | — | 4.6 | 20.5 | 15.7 |
| n $C_6$ | 5.8 | — | 1.7 | 13.8 | 20.4 |
| Methyl cyclo pentane | 1.9 | — | 0.5 | 4.4 | 10.2 |
| Cyclo $C_6$ | 1.9 | — | 0.3 | 3.5 | 25.8 |

TABLE III-continued

| Descrip-tion wt. % | Stream No. | | | | |
|---|---|---|---|---|---|
| | 23 Liquid Effluent | 25 Fuel Gas | 26 IZ Product | 27 DIHT Recycle Stream | 28 DIHT Heavy Stream |
| Benzene + | 0.4 | — | — | 0.5 | 6.7 |
| Relative mass flow rate | 44.8 | 1.8 | 27.8 | 14.2 | 1.0 |
| Volumetric flow rate B/D | 40,873 | — | 25,415 | 12,437 | 838 |

Where:
PFT = preflash tower
DIHT = de-isohexanizer tower
IZ = isomerization zone As can be seen from Examples I, and II use of a preflash tower allows the same stabilizer tower to be used for both once-through (Example II) and recycle operations (Example I). In the case of once-through operation, 27,996 barrels/day of liquid feed is passed to the stabilizer tower and in the case of recycle operations, 27,586 barrels/day of liquid feed is passed to the stabilizer tower.

If recycle operations were to be performed without the use of a preflash tower (as is shown in Example III) a larger stabilizer tower would be needed since its liquid feed rate would be about 40,873 barrels/day. Designing a single stabilizer tower to handle these two disparate flow rates would require compromises in tower performance for each flow rate.

I claim as may invention:

1. In a process for isomerization of a $C_5$ to $C_6$ feedstock comprising paraffins in which the feedstock is passed into an isomerization zone at reaction conditions to effect production of an effluent containing an isomerization product having an increased octane value, wherein the effluent is passed into a separation zone for removal of light gases from liquid effluent, the liquid effluent is fractionated into (1) a fuel gas stream, (2) isomerization zone product comprising iso $C_5$ and iso $C_6$ paraffins, (3) a recycle stream comprising $C_6$ paraffins and cycloparaffins having higher boiling points than the isomerization zone product, a part of which is passed into the isomerization zone as recycle material and (4) a heavy stream comprising $C_6$ and $C_7$ and higher having a boiling range higher than recycle material, wherein an improvement comprises: (A) passing at least a portion of liquid effluent into a preflash tower for separation into preflash overhead fraction comprising dimethylbutane, pentanes and lighter materials and a preflash bottoms fraction comprising dimethylbutane, pentanes and heavier materials, (B) passing at least a portion of the preflash bottoms fraction into a de-isohexanizer tower to separate said bottoms into a (i) de-isohexanizer overhead fraction comprising dimethylbutane, pentanes and lighter materials carried over into the de-isohexanizer column from the preflash tower, (ii) said recycle stream, and (iii) said heavy stream, (C) passing at least a portion of the preflash overhead fraction and the de-isohexanizer overhead fraction into a stabilizer tower to separate these fractions into (i) a feed gas stream comprising $C_4$ and lighter hydrocarbons and (ii) said isomerization zone product.

2. The process of claim 1 further characterized in that the liquid effluent comprises $C_5$ to $C_6$ hydrocarbons boiling in a range of from about 80° F. to about 170° F.

3. The process of claim 2 further characterized in that the isomerization zone product comprises $C_5$ to $C_6$ hydrocarbons boiling in a range of from about 120° F. to about 160° F.

4. The process of claim 1 further characterized in that the recycle material comprises $C_6$ hydrocarbons boiling in a range of from about 140° F. to about 160° F.

5. The process of claim 4 further characterized in that the heavy stream comprises $C_6$ to $C_7$ hydrocarbons boiling in a range of from about 150° F. to about 170° F. or higher.

6. In a process for isomerization of a $C_5$ to $C_6$ feedstock comprising paraffins in which the feedstock is passed into an isomerization zone at reaction conditions to effect production of an effluent containing an isomerization product having an increased octane value, wherein the effluent is passed into a separation zone for removal of light gases from liquid effluent, the liquid effluent is fractionated into (1) a fuel gas stream, (2) isomerization zone product comprising iso $C_5$ and iso $C_6$ paraffins, (3) a recycle stream comprising $C_6$ paraffins and cycloparaffins having higher boiling points than the isomerization zone product, a part of which is passed into the isomerization zone as recycle material and (4) a heavy stream comprising $C_6$ and $C_7$ and higher having a boiling range higher than recycle material, wherein an improvement comprises: (A) passing substantially all of the liquid effluent into a preflash tower for separation into a preflash overhead fraction comprising dimethylbutane, pentanes and lighter materials and a preflash bottoms fraction comprising dimethylbutane, pentanes and heavier materials, (B) passing substantially all of the preflash bottoms fraction into a de-isohexanizer tower to separate said bottoms into a (i) de-isohexanizer overhead fraction comprising dimethylbutane, pentanes and lighter materials carried over into the de-isohexanizer column from the preflash tower, (ii) said recycle stream, and (iii) said heavy stream, (C) passing substantially all of the preflash overhead fraction and the de-isohexanizer overhead fraction into a stabilizer tower to separate these fractions into (i) a fuel gas stream comprising $C_4$ and lighter hydrocarbons and (ii) said isomerization zone product.

* * * * *

UNITED STATES PATENT OFFICE
CERTIFICATE OF CORRECTION

Patent No. 4,831,209          Dated May 16, 1989

Inventor(s) LARRY W. KRUSE

It is certified that error appears in the above-identified patent and that said Letters Patent is hereby corrected as shown below:

| Col. | Line | |
|---|---|---|
| 3 | 34 | "tower and Figure 2" should be -- tower and Figure 2 -- |
| 7 | 34 | "di-isohexanizer" should be -- de-isohexanizer -- |
| 8 | 17 | "octance" should be -- octane -- |
| 11 | 31 | "may" should be -- my -- |

Signed and Sealed this

Sixth Day of February, 1990

*Attest:*

JEFFREY M. SAMUELS

*Attesting Officer*     *Acting Commissioner of Patents and Trademarks*